(12) United States Patent
Kado et al.

(10) Patent No.: US 7,736,883 B2
(45) Date of Patent: Jun. 15, 2010

(54) ADDITIVE FOR FEEDS AND FEED CONTAINING THE SAME

(75) Inventors: Yukiko Kado, Tokyo (JP); Masami Morotomi, Tokyo (JP)

(73) Assignee: Kabushiki Kaisha Yakult Honsha, Tokyo (JP)

(*) Notice: Subject to any disclaimer, the term of this patent is extended or adjusted under 35 U.S.C. 154(b) by 0 days.

(21) Appl. No.: 11/665,350

(22) PCT Filed: Oct. 13, 2004

(86) PCT No.: PCT/JP2004/015072

§ 371 (c)(1),
(2), (4) Date: Apr. 13, 2007

(87) PCT Pub. No.: WO2006/040816

PCT Pub. Date: Apr. 20, 2006

(65) Prior Publication Data

US 2007/0286888 A1    Dec. 13, 2007

(51) Int. Cl.
*C12N 1/20* (2006.01)
*C12N 1/00* (2006.01)
*A01N 63/00* (2006.01)

(52) U.S. Cl. .................. 435/252.4; 435/252.9; 435/853; 424/93.45

(58) Field of Classification Search ............ None
See application file for complete search history.

(56) References Cited

U.S. PATENT DOCUMENTS 6,537,544 B1 * 3/2003 Johansson et al. ........ 424/93.45

2004/0175372 A1  9/2004  Park et al.

FOREIGN PATENT DOCUMENTS

| JP | 02-138131 A | 5/1990 |
|---|---|---|
| JP | 2001-519144 A | 10/2001 |
| JP | 2003-235569 A | 8/2003 |
| WO | 99/18188 A1 | 4/1999 |
| WO | 02/05829 A3 | 1/2002 |
| WO | 2004/000335 A1 | 12/2003 |

OTHER PUBLICATIONS

Masami Morotomi et al., "*Lactobacillus equi* sp. Nov., a predominant intestinal *Lactobacillus* species of the horse isolated from faeces of healthy horses", International Journal of Systematic and Evolutionary Microbiology (2002), 52, 211-214.

Norikatsu Yuki et al., "Colonization of the Stratified Squamous Epithelium of the Nonsecreting Area of Horse Stomach by *Lactobacilli*", Applied and Environmental Microbiology, Nov. 2000, p. 5030-5034, vol. 66, No. 11.

Teruhiko Yuyama et al., "Uma yo ni Shinki Kaihatsu shita Seikin Seizai no Rinsho Koka", Journal of intestinal microbiology, Jul. 2004, vol. 18, No. 2, pp. 101 to 106.

* cited by examiner

*Primary Examiner*—Vera Afremova
(74) *Attorney, Agent, or Firm*—Sughrue Mion, PLLC

(57) ABSTRACT

An additive for feeds is provided which is efficacious in preventing and ameliorating digestive disorders such as diarrhea occurring as the side effects of the administration of antibiotics and a feed containing same. More specifically, an additive for feeds which comprises (A) *Lactobacillus equi* cells and (B) cells of at least one bacterium selected from the group consisting of *Lactobacillus salivarius*, *Lactobacillus crispatus* and *Lactbacillus johnsonii*.

5 Claims, 1 Drawing Sheet

ADDITIVE FOR FEEDS AND FEED CONTAINING THE SAME

TECHNICAL FIELD

The present invention relates to an additive for feeds to prevent and ameliorate digestive disorders occurring as side effects of the administration of antibiotics in rearing and management of horses and to a feed containing same.

BACKGROUND ART

In general, representative animals which are reared and managed as livestock include cattle, swine, horses, etc., and the growth processes and physical conditions of such livestock are susceptible to changes in rearing environments or the like, so the animals require sufficient attention in rearing and management. For example, horses are known to have tendencies to develop physical symptoms such as diarrhea induced by various types of stress due to changes in rearing environment such as feed. In the intestines of horses (in particular, foals), there are fewer bacteria compared to other livestock, and the bacteria suffer extreme decreases due to changes in rearing environment. Therefore, intestinal flora which create the ecosystem of intestinal bacteria are damaged, and the ecosystem is disturbed, resulting in occurrence of symptoms such as diarrhea. Such symptoms have an adverse effect on physiological functions such as decrease in digestion and absorption ability, inhibition of growth, and suppression of immune system, so it causes great damage to the race horse production field.

In recent years, feeds containing bacteria such as lactic bacteria and bifidobacteria have been widely used in rearing and management of horses (see, for example, Patent Documents 1 to 4). Those feeds may ameliorate intestinal flora and provide physiological effects such as growth promotion and diarrhea amelioration by adhesion of the bacteria in the feed to the intestines of horses.

However, even if those feeds are used, the administered bacteria do not adhere to and proliferate in the intestines of horses, and the effects of ameliorating physiological symptoms such as diarrhea are not sufficiently exerted in many cases. Therefore, in actuality, various antibiotics are now administered depending on the symptoms.

Although antibiotics to be administered may effectively ameliorate physical symptoms of horses, they may have effects such as killing bacteria present in the intestines of horses and cause side effects such as aggravation of diarrhea symptoms in many cases. Meanwhile, such antibiotics kill not only bacteria present in the intestines of horses but also useful bacteria that are separately administered as feed or the like, so even in the case where a feed containing useful bacteria as living bacteria is administered to horses, effects of the administered bacteria cannot be sufficiently achieved, and effects of ameliorating physical symptoms that cause digestive disorders such as diarrhea are low.

Therefore, for a feed containing bacteria to be used in the rearing and management of horses, it is necessary not only to select bacteria such as lactic bacteria and bifidobacteria that have the effect of ameliorating intestinal environments but also to select bacteria that exhibit specific adhesion to the digestive epithelia of a horse and proliferative activity and have excellent effects of improving intestinal environments of horses and to select bacteria that have excellent resistance to various antibiotics that may be administered as needed depending on the physical symptoms of horses.

Patent Document 1: Japanese Patent Laid-open No. 59-46208
Patent Document 2: Japanese Examined Patent application publication No. 3220699
Patent Document 3: Japanese Patent Laid-open No. 2001-519144
Patent Document 4: Japanese Patent Laid-open No. 2002-58432

DISCLOSURE OF THE INVENTION

Problems to be Solved by the Invention

Therefore, an object of the present invention is to provide an additive for feeds that exhibits specific adhesion to the digestive epithelia of horses and proliferative activity, has excellent resistance to antibiotics, and is efficacious in preventing and ameliorating digestive disorders such as diarrhea occurring as the side effects of the administration of antibiotics, and a feed containing same.

Means for Solving the Problems

The inventors of the present invention have made extensive studies, and as a result, they have found out that, among bacteria belonging to the genus *Lactobacillus*, five bacterial strains having excellent adhesion to the digestive epithelia of horses and proliferative activities have high diarrhea preventing/ameliorating effects for horses (in particular, foals) and has excellent resistance to antibiotics compared to other bacteria.

Meanwhile, they have found that the five bacterial strains belonging to the genus *Lactobacillus* exhibit excellent resistance to antibiotics and have different antibacterial spectrum although they belong to the same genus, thereby completing the present invention.

The present invention also provides an additive for feeds including (A) *Lactobacillus equi* cells and (B) cells of at least one bacterium selected from the group consisting of: *Lactobacillus salivarius*; *Lactobacillus reuteri*; *Lactobacillus crispatus*; and *Lactobacillus johnsonii*.

The present invention further provides an additive for feeds, further including (C) at least one antibiotic selected from the group consisting of: ceftriaxone sodium; kanamycin sulfate; dihydrostreptomycin; sulfamonomethoxine; Bactramin; gentamicin, ofloxacin; cefalotin sodium; ampicillin; oxytetracycline hydrochloride; and benzylpenicillin.

The present invention also provides an additive for feeds which is intended to be added in combination with the antibiotics (C).

According to the present invention, there is provided a feed including the additive for feeds.

In accordance with the present invention, there is provided at least one bacterial strain belonging to the genus *Lactobacillus* selected from the group consisting of the following (i) to (iv):

(i) *Lactobacillus salivarius* YIT0479 strain (accession number: FERM BP-10095);

(ii) *Lactobacillus reuteri* YIT0480 strain (accession number: FERM BP-10096);

(iii) *Lactobacillus crispatus* YIT0481 strain (accession number: FERM BP-10097); and (iv) *Lactobacillus johnsonii* YIT0482 strain (accession number: FERM BP-10098).

Effect of the Invention

The present invention provides an additive for feeds that exhibits specific adhesion to the digestive epithelia of horses and proliferative activity, has excellent resistance to antibiotics, and is efficacious in preventing and ameliorating digestive disorders such as diarrhea occurring as the side effects of the administration of antibiotic, and a feed containing same.

BEST MODE FOR CARRYING OUT THE INVENTION

Figure 1:
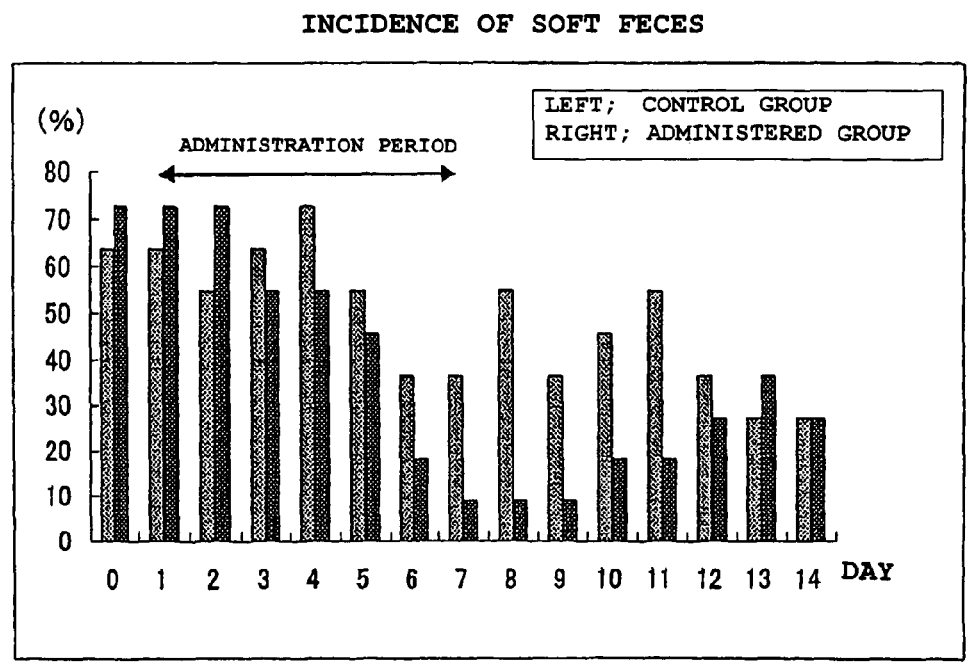
FIG. 1 A graph showing the incidence rates of soft feces in foals of a group administered with the additive for feeds and a control group in Example 5.

An additive for feeds of the present invention includes: (A) *Lactobacillus equi* cells and (B) cells of at least one bacterium selected from the group consisting of *Lactobacillus salivarius, Lactobacillus reuteri, Lactobacillus crispatus*, and *Lactobacillus johnsonii*.

All five bacterial strains to be used in the present invention belong to the genus *Lactobacillus* and are isolated from the feces of horses. The strains are isolated by culturing at about 37° C. under anaerobic conditions using an LBS medium as a selective medium for *Lactobacillus* bacteria and an MRS medium as a nonselective medium. The isolated bacterial strains are characterized by morphometric properties, culture properties, physiological properties, chemotaxonomical properties, etc. Among bacteria belonging to the genus *Lactobacillus*, the above-described bacterial strains exhibit particularly excellent adhesion to the digestive epithelia of horses and proliferative activities and have excellent resistance to antibiotics.

As bacterial strains of (A) *Lactobacillus equi*, the *L. equi* YIT0483 strain (deposited to National Institute of Advanced Industrial Science and Technology on Jan. 16, 2002, Accession No. "FERM BP-10094") is particularly preferable because of excellent adhesion and proliferative activity.

Meanwhile, the (B) four *Lactobaciilus* bacterial strains (i) *Lactobacillus salivarius* YIT0479 strain (deposited to National Institute of Advanced Industrial Science and Technology on May 6, 2003, Accession No: "FERM BP-10095") ; (ii) *Lactobacillus reuteri* YIT0480 strain (deposited to National Institute of Advanced Industrial Science and Technology on May 6, 2003, Accession No: "FERM BP-10096"); (iii) *Lactobacillus crispatus* YIT0481 strain (deposited to National Institute of Advanced Industrial Science and Technology on May 6, 2003, Accession No: "FERM BP-10097"); and (iv) *Lactobacillus johnsonii* YIT0482 strain (deposited to National Institute of Advanced Industrial Science and Technology on May 6, 2003, Accession No: "FERM BP-10098") are particularly preferable because all of them have excellent resistance to antibiotics.

The above-described (B) four *Lactobacillus* bacterial strains, (i) *Lactobacillus salivarius* YIT0479 strain, (ii) *Lactobacillus reuteri* YIT0480 strain, (iii) *Lactobacillus crispatus* YIT0481 strain, and (iv) *Lactobacillus johnsonii* YIT0482 strain are newly isolated bacterial strains, and (a) morphometric properties, (b) culture properties, and (c) chemotaxonomical properties, etc. are therefore shown below. Note that the four bacterial strains (i) to (iv) of the present invention have no significant differences in the properties (a) to (c) of the strains.

(a) Morphometric Properties

All four bacterial strains (i) to (iv) of the present invention have the following properties. Meanwhile, Gram stain images of all the four bacterial strains (i) to (iv) above are positive.

(1) Shape of bacterium: bacillary form (2) Size of bacterium: 0.6 to 0.8·1.3 to 3.5 μm (3) Polymorphism of bacterium: none (4) Mobility: none (5) Spore: none Gram-stain images reveal that: (i) *L. salivarius* YIT0479 strain bacteria are bacilli having a uniform size; (ii) *L. reuteri* YIT0480 strain bacteria are short bacilli having a uniform size; and (iii) *L. crispatus* YIT0481 strain bacteria and (iv) *L. johnsonii* YIT0482 strain bacteria are bacilli having uniform sizes (slightly thin).

(b) Culture Properties (Growing States)

(1) Growing states of the four bacterial stains (i) to (iv) of the present invention in MRS agar plate culture (37° C., 2 days) will be described below.

(i) *L. salivarius* YIT0479 strain forms white smooth spherical colonies with a diameter of about 1 mm. (ii) *L. reuteri* YIT0480 strain forms white smooth spherical colonies with a diameter of about 2 mm. (iii) *L. crispatus* YIT0481 strain forms grayish-white rough flat colonies with a diameter of about 2 mm. (iV) *L. johnsonii* YIT0482 strain forms grayish-white smooth flat colonies with a diameter of about 1 mm.

(2) The growing states of all the four bacterial stains (i) to (iv) of the present invention in MRS agar plate culture (37° C., 2 days) were good, and precipitates were formed when the strains were allowed to stand.

(c) Chemotaxonomical Properties (Determination of GC Content and DNA-DNA Hybridization)

Determination of the GC contents of the four bacterial strains (i) to (iv) of the present invention and DNA-DNA hybridization between the four strains and standard strains of related bacterial strains were performed in accordance with the following methods.

The GC contents can be determined by a method by Ezaki et al. using conventional high performance liquid chromatography (document name: FEMS Microbiol Lett 55, 127-130, 1990). The determined GC contents of the four bacterial strains (i) to (iv) of the present invention are 33 to 41 mol %.

DNA-DNA hybridization can be performed by ordinary methods, i.e., fluorescence-labeling microplate method (document name: Int J Syst Bacteriol 39, 224-229, 1989). The following 20 standard strains (which all belong to the genus *Lactobacillus*) are used for comparison to the four bacterial strains (i) to (iv) of the present invention. The four bacterial strains (i) to (iv) of the present invention are separately identified by the standard strains having homologies.

*L. acidophilus* YIT 0070 (ATTC 4356$^T$), *L. agilis* YIT 0253 (JCM 1187$^T$), *L. amylovorus* YIT 0211 (JCM 1126$^T$), *L. animalis* YIT 0256 (JCM 5670$^T$), *L. brevis* YIT 0076 (ATTC 14869$^T$), *L. buchneri* YIT0077 (ATTC4005$^T$), *L. casei* YIT0180 (ATTC344$^T$), *L. coryniformis* subsp. *coryniformis* YIT 0237 (JCM 1164$^T$), *L. crispatus* YIT 0212 (JCM 1185$^T$), *L. fermentum* YIT 0081 (ATTC 14931$^T$), *L. gasseri* YIT 0192 (DSM 20243$^T$), *L. graminis* YIT 0260 (NRIC 1775$^T$), *L. johnsonii* YIT 0219 (JCM 2012$^T$), *L. murinus* YIT 0239 (JCM 1717$^T$), *L. plantarum* YIT 0102 (ATTC 14917$^T$), *L.*

*reuteri* YIT 0197 (JCM 1112$^T$), *L. rhamnosus* YIT 0105 (ATTC7469$^T$), *L. ruminis* YIT 0221 (JCM1152$^T$), *L. salivarius* subsp. *salicinius* YIT 0089 (ATTC 11742$^T$), and *L. salivarius* subsp. *salivarius* YIT 0104 (ATTC 11741$^T$).

Cells in an additive for feeds of the present invention have excellent resistance to various antibiotics, so they may be added to feeds as mixtures of the cells and various antibiotics if necessary for healthcare of horses. Meanwhile, an additive for feeds including only cells may be singly added to feeds or may be added in combination with various antibiotics. As described above, the additive for feeds is efficacious for healthcare and amelioration of physical symptoms of horses because various antibiotics can be appropriately selected depending on physical symptoms of horses to be combined for all cases.

(C) Antibiotics to be used in the present invention may be ones generally used for healthcare of horses, and examples thereof include: gentamicin, oxytetracycline hydrochloride, etc. which are effective for diarrhea and diarrhea alba symptoms of foals; kanamycin sulfate, sulfamonomethoxine, Bactramin, ceftriaxone sodium, cefalotin sodium, ofloxacin, dihydrostreptomycin, etc. which are effective for various infectious diseases due to pneumonia and arthritis; and benzylpenicillin, ampicillin, etc. which are effective for protection against infectious diseases due to injury, protection against shipping fever, and protection against hives.

Among the above-described (C) antibiotics, which one to use is determined depending on the type of selected (B) *Lactobacillus* bacterium. For example, kanamycin sulfate, sulfamonomethoxine, Bactramin, etc. may be used for all of the (B) four *Lactobacillus* bacterial strains. Meanwhile, ofloxacin may be used for (B) *Lactobacillus reuteri*, *Lactobacillus crispatus*, and *Lactobacillus johnsonii*. Moreover, cefalotin sodium, oxytetracycline hydrochloride, benzylpenicillin, ampicillin, etc. may be used for (B) *Lactobacillus reuteri*.

Next, a method of producing an additive for feeds will be described.

An additive for feeds is produced as follows: (A) *Lactobacillus equi* strains and (B) strains of at least one bacterium selected from the group consisting of *Lactobacillus salivarius, Lactobacillus reuteri, Lactobacillus crispatus*, and *Lactobacillus johnsonii* are separately cultured, and the cultured cells are collected, followed by mixing of (A) cells and (B) cells.

The above-described culture and collection can be performed by ordinary methods. Examples of a medium to be used include an MRS broth (manufactured by Difco Laboratories) medium and an GAM broth (manufactured by Nissui) medium in which *Lactobacillus* bacteria can be proliferated. All the bacterial strains are cultured under conditions of 37° C. for 12 to 20 hours. The cells can be collected by generally used means such as centrifugation. The resultant additive for feeds may be formed into an appropriate shape depending on the purpose of use.

In the above-described production method, the degree of proliferation of the respective bacterial strains differ, so it is desired to culture the strains using not only the above-described mediums but also mediums optimal for the respective bacterial strains. For example, for *Lactobacillus reuteri* YIT0480 strain, PSYL medium (composition: 20% PSM*) 5%, Myeast P2G (Nihon Pharmaceutical Co., Ltd,) 1%, CH$_3$COONa (manufactured by Wako Pure Chemical Industries, Ltd.) 0.3%, (NH$_4$)$_2$SO$_4$ (manufactured by wako Pure Chemical Industries, Ltd.) 0.3%, KH$_2$PO$_4$ (manufactured by Wako Pure Chemical Industries, Ltd.) 1%, K$_2$HPO$_4$ (manufactured by Wako Pure Chemical Industries, Ltd.) 0.2%, Met sol**) 0.5%) is preferable.

*): skim milk (Yotsuba Inc.) 200 g, orientase 5 N (Hankyu Bioindustry Co., Ltd.) 4 g/1 L

**): MgSO$_4$.7H$_2$O 115 g, FeSO$_4$.7H$_2$O 6.8 g, MnSO$_4$.7H$_2$O (manufactured by Wako Pure Chemical Industries, Ltd.) 24 g/1 L Meanwhile, to improve proliferation abilities of the bacterial strains, it is desirable to add an assimilating sugar to the mediums, if necessary. For example, in the cases of *Lactobacillus equi* YIT0483 strain and *Lactobacillus crispatus* YIT0481 strain, lactose is preferably added to a medium as an assimilating sugar. Meanwhile, in the cases of *Lactobacillus salivarius* YIT0479 strain and *Lactobacillus johnsonii* YIT0482 strain, glucose is preferably added to a medium as an assimilating sugar.

In the present invention, mediums to be used are not limited to the above-described mediums, and there may be used mediums optimal for the respective bacterial strains, which are prepared by appropriately combining compositions in generally used mediums.

The cells to be used for an additive for feeds of the present invention are desirably living cells, and they may be in any state as long as they are living cells. For example, they may be cultured collected cells, cultures, freeze-dried cells, etc. of the respective bacterial strains. Among them, it is desirable to use freeze-dried cells because living cells have high storage stability. Further, dead cells are not preferable because they have low physiological effects such as prevention and amelioration of digestive disorders including diarrhea and promotion of early intestinal flora formation when administered to horses.

An additive for feeds of the present invention exhibits excellent adhesion to gastric mucosal epithelial cells of horses and proliferative activity and has excellent resistance to antibiotics. The additive for feeds can therefore prevent and ameliorate digestive (in particular, intestinal) disorders of horses such as diarrhea by a rising from early formation of intestinal flora, can preferably maintain digestive environments of horses in good states without effects of the above-described (C) antibiotics that sometimes need to be used for the healthcare of horses, and can effectively improve the physical symptoms of horses induced by various type of stress. Moreover, in the present invention, an additive for feeds containing (A) *Lactobacillus equi* cells and (B) cells of all the four *Lactobacillus* bacteria is particularly preferable because it has significant effects in ameliating the above-described physical symptoms of horses.

An additive for feeds of the present invention is preferably administered in an amount of 1·10$^9$ cells or more, more preferably 1·10$^{10}$ cells to 5·10$^{10}$ cells as the number of total cells of the above-described (A) and (B) per horse per day. If the additive is administered in an amount of less than 1·10$^9$ cells per day, physical symptoms of horses are not sufficiently improved, which is undesirable. Moreover, the proportion of the cell numbers of the respective bacterial strains in an additive for feeds to be administered may be arbitrarily adjusted depending on the combination of bacterial strains to be contained in the additive for feeds, and an additive for feeds containing (A) *Lactobacillus equi* at a rate in the range of 5% to 25%, preferably 10% to 20%, with respect to the total number of cells has significant effect in ameliorating the physical symptoms of horses.

Meanwhile, the method of administering an additive for feeds of the present invention to horses is not particularly limited, and the additive may be administered directly to the intestines of horses using an injection or may be administered orally as a preparation such as powders, tablets, granules, or pellets produced by conventional methods together with various sugars, proteins, lipids, fibers, vitamins, minerals, etc.

The present invention provides a feed containing such an additive for feeds and another component such as lipids or fibers. The lipids and fibers are not particularly limited as long as they can be generally used as components for feeds, and examples thereof include soybean cake, alfalfa meal, and bran. Administration of a feed of the present invention can prevent and ameliorate digestive disorders and can improve feed efficiency, so the feed is preferable from the viewpoint of race horse management.

EXAMPLES

Hereinafter, the present invention will be described in more detail by way of examples, but it is not limited thereto.

Production Example 1

Production of Cells of Respective Bacterial Strains

Mediums (4.5 L each) having compositions shown in Table 1 below were prepared in 5 L-flasks and adjusted to pH 6.8, followed by high-pressure heat sterilization. Subsequently, the Klett values of precultured cells of five *Lactobacillus* strains (A) and (B) shown in Table 1 below were determined, and 450 ml of bacterial solutions diluted to Klett 300 were inoculated into the above-described mediums, followed by static culture at 37° C. for 16 hours, to thereby yield culture solutions. The culture solutions were centrifuged at 1,500·G, and the cells of the five bacterial strains were separately collected. The amounts (wet weights) of the collected cells per 4.5 L of the cells of the bacterial strains are shown in Table 1.

TABLE 1

| Composition of medium | | Inoculated strain | Amount of collected cells |
|---|---|---|---|
| 20% PSM*) | 5% | (B) | 93 g |
| Myeast P2G (Ninon Pharmaceutical Co., Ltd,) | 1% | *L. reuteri* YIT0480 strain | |
| $CH_3COONa$ | 0.3% | | |
| $(NH_4)_2SO_4$ | 0.3% | | |
| $KH_2PO_4$ | 1% | | |
| $K_2HPO_4$ | 0.2% | | |
| Met sol**) | 0.5% | | |
| Glucose | 2% | | |
| Proteose peptone No. 3 (Difco) | 1% | (A) | 94 g |
| Yeast extract D-3 (Difco) | 0.5% | *L. equi* YIT0483 strain | |
| Ammonium citrate | 0.2% | | |
| $CH_3COONa$ | 0.8% | | |
| $K_2HPO_4$ | 0.2% | (B) | 94 g |
| Met sol**) | 0.5% | *L. crispatus* YIT0481 strain | |
| Tween 80 (Tokyo Chemical Industry Co., Ltd.) | 0.1% | | |
| Lactose | 2% | | |
| Proteose peptone No. 3 (Difco) | 1% | (B) | 84 g |
| Yeast extract D-3 (Difco) | 0.5% | *L. salivarius* YIT0479 strain | |
| Ammonium citrate | 0.2% | | |
| $CH_3COONa$ | 0.8% | | |
| $K_2HPO_4$ | 0.2% | (B) | 94 g |
| Met sol**) | 0.5% | *L. johnsonii* YIT0482 strain | |
| Tween 80 (Tokyo Chemical Industry Co., Ltd.) | 0.1% | | |
| Glucose | 2% | | |

*)(skim milk (Yotsuba Inc.) 200 g, orientase (Hankyu Bioindustry Co., Ltd.) 4 g)/1 L
**)($MgSO_4 \cdot 7H_2O$) 115 g, $FeSO_4 \cdot 7H_2O$ 6.8 g, $MnSO_4 \cdot 7H_2O$ 24 g)/1 L Example 1

Proliferative Activity Test and Cell Adhesion Test to Horse Gastric Mucosal Epithelial Cell Four mediums, i.e., 10% skim milk (SM), 0.1% yeast extract (manufactured by Difco)+10% skim milk (YE), 0.1% peptone (manufactured by Difco)+10% skim milk (P), and 0.1% yeast extract (manufactured by Difco)+0.1% peptone (manufactured by Difco)+10% skim milk (YP) were subjected to high-pressure heat sterilization at 115° C. for 15 minutes, and then cell culture solutions of the five bacterial stains (A) and (B) obtained in Production Example 1 above (30 μl each) were separately inoculated into 3 ml of the respective mediums (the cell number of each bacterial strain: about $3 \cdot 10^8$ cells/ml), followed by culture at 37° C. for 24 hours and 48 hours. For proliferative activity tests, the culture solutions were evaluated based on the following criteria: completely solidified culture solution due to proliferated cells: "○"; semifluid culture solution with slightly proliferated cells: "Δ"; and liquid culture solution with unproliferated cells: "x".

Meanwhile, gastric mucosal epithelial tissue pieces (1 $cm^2$) taken from a horse were added to 3 ml (the cell number of each bacterial strain: about $3 \cdot 10^8$ cells/ml) of cell culture solutions of the five bacterial stains (A) and (B) obtained in Production Example 1 above, followed by culture with shaking at 37° C. Then, the gastric mucosal epithelial tissue pieces were washed with a buffer (composition: 0.8% NaCl; 0.121% $K_2HPO_4$; 0.034% $KH_2PO_4$; pH 7.2) several times, and the gastricmucosal epithelial cells were scraped off from the gastric mucosal epithelial tissue pieces under a stereomicroscope, followed by Giemsa stain. The resultant cells were used to count the number of cells of each bacterial strain that adhered to one gastric mucosal epithelial cell under a microscope, and the adhesion was evaluated. The results are shown in Table 2.

TABLE 2

Table 2: Proliferative activity and adhesion

| Bacterial strain | Proliferative activity | | | | | | | | Adhesion of bacteria to horse gastric mucosal epithelial cell |
|---|---|---|---|---|---|---|---|---|---|
| | 24 hours later | | | | 48 hours later | | | | |
| | SM | YE | P | YP | SM | YE | P | YP | |
| (A) *L. equi* YIT0483 strain | ○ | ○ | ○ | ○ | ○ | ○ | ○ | ○ | ++ |
| (B) *L. salivarius* YIT0479 strain | x | ○ | ○ | ○ | ○ | ○ | ○ | ○ | ++ |
| (B) *L. reuteri* YIT0480 strain | x | ○ | ○ | ○ | x | ○ | ○ | ○ | + |
| (B) *L. crispatus* YIT0481 strain | x | ○ | ○ | ○ | ○ | ○ | ○ | ○ | + |
| (B) *L. johnsonii* YIT0482 strain | x | ○ | ○ | ○ | x | ○ | ○ | ○ | + |

++: 10-99 cells adhered to one gastric mucosal epithelial cell
+: 1-9 cells adhered to one gastric mucosal epithelial cell As is clear from the results shown in Table 2, the cells of the respective five *Lactobacillus* bacterial stains (A) and (B) used in the present invention were found to exhibit excellent proliferative activities under the respective medium conditions and exhibit good adhesion to horse gastric mucosal epithelial cells. Meanwhile, among the five bacterial strains, (A) *L. equi* YIT0483 strain was found to have excellent proliferative activity and adhesion to horse gastric mucosal epithelial cells compared to the other four bacterial strains (B). Note that, in the proliferative activity test, there was no semifluid culture solution with slightly proliferated cells (evaluation: Δ).

Example 2

Antibiotic Resistance Test

The 11 antibiotics shown in Table 3 were separately added at concentrations of 100, 10, 1, 0.1, and 0 μg/ml, to thereby prepare MRS agar mediums (manufactured by Difco). Subsequently, cell culture solutions of the five bacterial stains (A) and (B) obtained in Production Example 1 (10 μl each) were separately inoculated into the respective antibiotic-containing MRS mediums (the cell number of each bacterial strain: about $1 \cdot 10^8$ cells/ml), followed by smear culture at 37° C. for 48 hours under anaerobic conditions. The proliferated bacteria were evaluated with the naked eye, and the minimum growth rates for each antibiotic (μg/ml) were calculated. The results are shown in Table 3.

TABLE 3

Table 3: Antibiotic resistance test

| Bacteria | Minimum growth rate (μg/ml) | | | |
|---|---|---|---|---|
| | 100≧ | 100 | 10 | 1 |
| (A) *L. equi* YIT0483 strain | Ceftriaxone sodium Kanamycin sulfate Dihydrostreptomycin Sulfamonomethoxine Bactramin | Gentamicin Ofloxacin | Cefalotin sodium Ampicillin Oxytetracycline hydrochloride | Benzylpenicillin |
| (B) *L. salivarius* YIT0479 strain | Kanamycin sulfate Sulfamonomethoxine Dihydrostreptomycin Bactramin | Gentamicin Ofloxacin | Ceftriaxone sodium Cefalotin sodium Ampicillin Oxytetracycline hydrochloride | Benzylpenicillin |
| (B) *L. reuteri* YIT0480 strain | Kanamycin sulfate Sulfamonomethoxine Ofloxacin Bactramin Dihydrostreptomycin | Ceftriaxone sodium Ampicillin Gentamicin Cefalotin sodium Oxytetracycline hydrochloride | Benzylpenicillin | |
| (B) *L. crispatus* YIT0481 strain | Kanamycin sulfate Sulfamonomethoxine Ofloxacin Bactramin | Gentamicin | Ceftriaxone sodium Cefalotin sodium Ampicillin Oxytetracycline | Benzylpenicillin |

TABLE 3-continued

Table 3: Antibiotic resistance test

| | Minimum growth rate (µg/ml) | | | |
|---|---|---|---|---|
| Bacteria | 100≧ | 100 | 10 | 1 |
| (B) L. johnsonii YIT0482 strain | Dihydrostreptomycin Kanamycin sulfate Sulfamonomethoxine Gentamicin Ofloxacin Bactramin | Dihydrostreptomycin | hydrochloride Ceftriaxone sodium Cefalotin sodium Ampicillin Oxytetracycline hydrochloride | Benzylpenicillin |

As is clear from the results shown in Table 3, the respective five *Lactobacillus* bacterial stains (A) and (B) were found to exhibit excellent resistance to various antibiotics, in particular, kanamycin sulfate, sulfamonomethoxine, dihydrostreptomycin, Bactramin, etc. In particular, *L. equi* strain exhibited excellent specific resistance to ceftriaxone sodium; *L. johnsonii* strain exhibited excellent specific resistance to gentamicin; and *L. reuteri* strain, *L. crispatus* strain, and *L. johnsonii* strain exhibited excellent specific resistance to ofloxacin. Thus, the used five bacterial strains exhibited different antibacterial spectra although they belong to the same genus. Among the five bacterial strains, *L. reuteri* strain has particularly excellent resistance particularly to cefalotin sodium, oxytetracycline hydrochloride, and ampicillin. Such *L. reuteri* strain has stronger resistance to benzylpenicillin compared to the other four bacterial strains, so it is particularly useful in the case of using benzylpenicillin.

Meanwhile, the proliferative activity test in the presence of an antibiotic was performed using cell culture solutions containing (A) *L. equi* YIT0483 strain and (B) at least one selected from the four *Lactobacillus* strains in combination.

(Proliferative Activity Test 1)

MRS agar mediums (manufactured by Difco) to which oxytetracycline hydrochloride was added as an antibiotic at concentrations of 10, 5, 2, and 0 82 g/ml were prepared. Subsequently, a cell culture solution of only (A) *L. equi* strain and a mixed cell culture solution of (A) *L. equi* strain and (B) *L. reuteri* strain (10 µl each) were separately inoculated into the respective antibiotic-containing MRS mediums (the cell number of each bacterial strain: about 1·10$^6$ cells/ml), followed by smear culture at 37° C. for 48 hours under anaerobic conditions. Then, the proliferative activities of the bacteria were evaluated with the naked eye.

(Proliferative Activity Test 2)

MRS agar mediums (manufactured by Difco) to which gentamicin was added as an antibiotic at concentrations of 100, 50, 20, and 0 µg/ml were prepared. Subsequently, a cell culture solution of only (A) *L. equi* strain and a mixed cell culture solution of (A) *L. equi* strain and (B) *L. johnsonii* strain (10 µl each) were separately inoculated into the respective antibiotic-containing MRS mediums (the cell number of each bacterial strain: about 1·10$^6$ cells/ml), followed by smear culture at 37° C. for 48 hours under anaerobic conditions. Then, the proliferative activities of the bacteria were evaluated with the naked eye.

(Proliferative Activity Test 3)

MRS agar mediums (manufactured by Difco) to which ofloxacin was added as an antibiotic at concentrations of 100, 50, 20, and 0 µg/ml were prepared. Subsequently, a cell culture solution of only (A) *L. equi* strain and a mixed cell culture solution of (A) *L. equi* strain and (B) *L. johnsonii* strain or *L. equi* strain and *L. crispatus* strain (10 µl each) were separately inoculated into the respective antibiotic-containing MRS mediums (the cell number of each bacterial strain: about 1·10$^6$ cells/ml), followed by smear culture at 37° C. for 48 hours under anaerobic conditions. Then, the proliferative activities of the bacteria were evaluated with the naked eye. The results of proliferation activity tests 1 to 3 as described above are shown in Tables 4-1 to 4-3.

TABLE 4

1

| | Oxytetracycline (µg/ml) | | | |
|---|---|---|---|---|
| | 0 | 2 | 5 | 10 |
| Only (A) *L. equi* strain | ○ | x | x | x |
| Combination of (A) *L. equi* strain and (B) *L. reuteri* strain | ○ | ○ | ○ | ○ |

2

| | Genatmicin (µg/ml) | | | |
|---|---|---|---|---|
| | 0 | 20 | 50 | 100 |
| Only (A) *L. equi* strain | ○ | Δ | x | x |
| Combination of (A) *L. equi* strain and (B) *L. johnsonii* strain | ○ | ○ | ○ | x |

3

| | Ofloxacin (µg/ml) | | | |
|---|---|---|---|---|
| | 0 | 20 | 50 | 100 |
| Only (A) *L. equi* strain | ○ | x | x | x |
| Combination of (A) *L. equi* strain and (B) *L. johnsonii* strain | ○ | ○ | ○ | Δ |
| Combination of (A) *L. equi* strain and (B) *L. crispatus* strain | ○ | ○ | ○ | ○ |

Evaluation criteria of results:
○: fully proliferated
Δ: slightly proliferated
x: unproliferated As is clear from the results shown in Tables 4-1 to 3, use of a cell culture solution containing (A) *Lactobacillus equi* YIT0483 strain and (B) at least one selected from the four Lactobacillus strains having different antibacterial spectra in combination results in excellent proliferative activity even in the presence of an antibiotic.

Production Example 2

Production of Freeze-Dried Cells

Cell culture solutions of the five bacterial stains (A) and (B) obtained in Production Example 1 were separately adjusted to pH 6.8 to 7.0 with 10 N sodium hydroxide. Subsequently, the solutions were centrifuged at 5,000 rpm for 10 minutes to remove the supernatants, and a dispersion medium (composition: an aqueous solution of skim milk 20% and trehalose 20%) was added to the resultant cells at a rate of 8%, followed by homogenization. Thereafter, the cells were subjected to prior freezing at −30° C. for 3 hours and then to a freeze-drying treatment in accordance with conventional methods. After freeze-drying, the cells were weighed, and equal amounts of dried starch was added thereto, followed by storing at 4° C.

Example 3

Early Intestinal Flora Formation Promoting Effect

A solution prepared by dissolving 5 g of the freeze-dried cells obtained in Production Example 2 (containing living cells of the five *Lactobacillus* bacterial strains (A) and (B) in an amount of $3.8 \cdot 10^{10}$ cells/5 g in total) in 50 ml of 5% glucose was orally administered to six newborn thoroughbred foals everyday a total of seven times. Rectal feces were collected 1, 2, 3, 5, 7, and 14 days after birth, and a diluent was added thereto, followed by homogenization. The resultant homogenates were further appropriately diluted and inoculated into LBS agar mediums (manufactured by Becton, Dickinson and Company), followed by culture under anaerobic conditions at 37° C. for 4 days, and the numbers of *Lactobacillus* bacteria in the rectal feces were calculated from the numbers of proliferated colonies and dilution rates. As a control group, the numbers of *Lactobacillus* bacteria in the rectal feces from six foals to which the freeze-dried cells had not been administered were calculated in the same way as above. Note that Table 5 shows the detection rates (%) calculated from the following expression: (the number of foals where *Lactobacillus* bacteria were detected)/(the number of all tested foals)·100.

TABLE 5

| After birth | Detection rate of Lactobacillus bacteria of control group | Detection rate of Lactobacillus bacteria of administered group |
|---|---|---|
| 1 day | 0% | 16.7% |
| 2 days | 25% | 66.7% |
| 3 days | 60% | 83.3% |
| 5 days | 66.7% | 100% |
| 7 days | 100% | 100% |
| 14 days | 100% | 100% |

As is clear from the results shown in Table 5, *Lactobacillus* bacteria were found to adhere in the intestines of all the foals of the administered group after five days of administration, and the intestinal flora formation promoting effect was seen two days early compared to the control group.

Example 4

Diarrhea Ameliorating Effect

Examination 1

Tests similar to those in Example 3 above were performed for 54 newborn foals (control group: 27 foals, administered group: 27 foals), and the occurrence of diarrhea was observed up to 30 days after birth. The diarrhea symptoms were grossly classified into three levels: soft feces, mild diarrhea (a foal which eliminates diarrhea stool less frequently and has slight adhesion of feces in the vicinity to the anus), and severe diarrhea (a foal which eliminates malodorous watery diarrhea stool on many occasions and has adhesion of a large volume of diarrhea stool in the region from the anus to the rump), and the incidence rates (%) of the respective symptoms are shown in Table 6.

TABLE 6

| | Control group | | | | Administered group | | | |
|---|---|---|---|---|---|---|---|---|
| Symptom | First week | Second week | Third week | Fourth week | First week | Second week | Third week | Fourth week |
| Soft feces | 23.1% | 57.7% | 42.3% | 15.4% | 33.3% | 59.3% | 14.8% | 18.5% |
| Mild diarrhea | 19.2% | 53.8% | 23.1% | 7.7% | 18.5% | 59.3% | 7.4% | 3.7% |
| Severe diarrhea | 3.8% | 11.5% | 11.5% | 3.8% | 7.4% | 7.4% | 0.0% | 0.0% |
| Curative treatment rate* | 3.8% | 11.5% | 11.5% | 3.7% | 7.4% | 7.4% | 3.7% | 0.0% |
| Antibiotic usage rate** | 3.8% | 3.8% | 3.8% | 7.7% | 7.4% | 7.4% | 3.7% | 0.0% |

*Curative treatment rate = (Number of treated foals)/(Number of all tested foals) × 100
**Antibiotic usage rate = (Number of antibiotic-administered foals)/(Number of all tested foals) × 100

As is clear from the results shown in Table 6, the incidence rates of soft feces of the administered group were found to decrease to a significantly low level in the third week. Meanwhile, the incidence rates of mild diarrhea and severe diarrhea tend to be significantly lower in the third week or later. In particular, the foals of the administered group did not develop severe diarrhea, and in the fourth week, the ameliorating effect was seen, resulting in no need for curative treatment or administration of antibiotics.

Example 5

Diarrhea Ameliorating Effect

Examination 2

A solution prepared by dissolving 5 g of the freeze-dried cells obtained in Production Example 2 (containing living cells of the five *Lactobacillus* bacterial strains (A) and (B) in an amount of $1.4 \cdot 10^{10}$ cells/5 g in total) in 50 ml of 5% glucose was orally administered to 22 thoroughbred foals in the administration period from day 1 to day 7 seven times in total per day. From day 0 (no administration) to day 14, the occurrence of diarrhea was observed. As a control group, for six foals to which the freeze-dried cells were not administered, the occurrence of diarrhea was observed. The diarrhea symptoms were grossly classified into two levels: soft feces and severe diarrhea (a foal which eliminates malodorous watery diarrhea stool on many occasions and has adhesion of a large volume of diarrhea stool in the region from the anus to the rump). The incidence rates of soft feces (%) and the incidence rates of severe diarrhea (%) are shown in FIG. 1 and FIG. 2, respectively.

Figure 2:
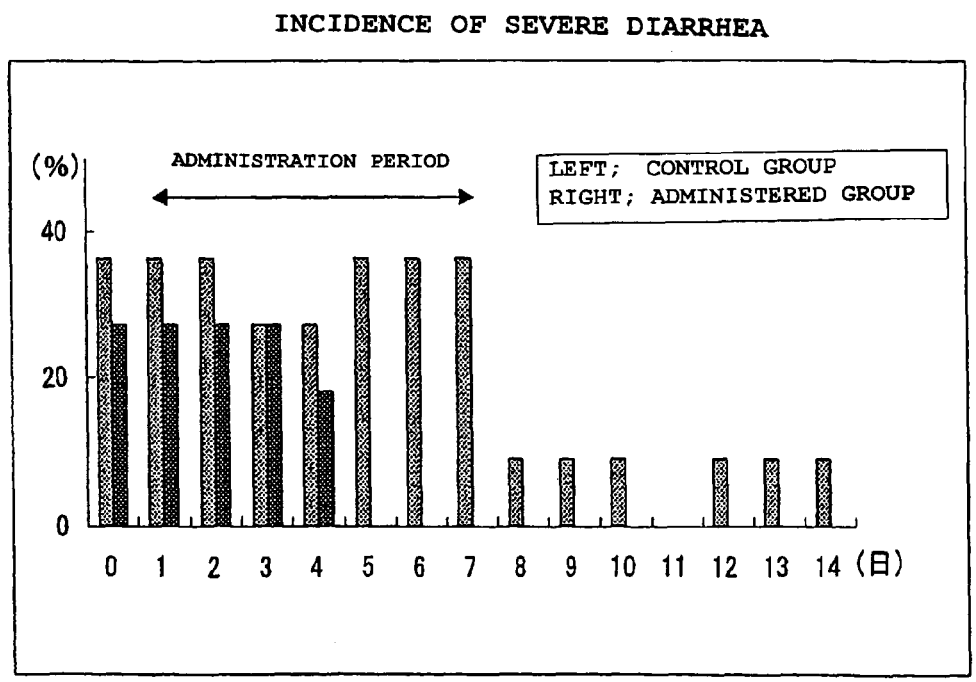
FIG. 2 A graph showing the incidence rates of severe diarrhea in foals of a group administered with the additive for feeds and a control group in Example 5.

As is clear from the results shown in FIGS. 1 and 2, the incidence rate of soft feces of the administered group tends to significantly decrease on the sixth day of administration compared to the control group. Meanwhile, the control group developed diarrhea symptoms, but the administration group was found not to develop diarrhea symptoms five days or later after administration.

INDUSTRIAL APPLICABILITY

The present invention can provide an additive for feeds that exhibits specific adhesion to the digestive epithelia of horses and proliferative activity, has excellent resistance to antibiotics, and is efficacious in preventing and ameliorating digestive disorders such as diarrhea occurring as side effects of the administration of antibiotics, and a feed containing same. Moreover, the present invention is useful in the rearing of livestock, in particular, in rearing and management of horses.

| | | |
|---|---|---|
| 0-1 | Form-PCT/RO/134 (SAFE) | |
| 0-1-1 | Description regarding the deposited bacteria or other biological materials (PCT Rule 13.2) created according to stipulations to right. | JPO-PAS 0321 |
| 0-2 | International application number | |
| 0-3 | Document symbol of applicant or attorney | FPI-12088 |
| 1 | The following descriptions relate to the bacteria or biological materials described in detailed description of the invention. | |
| 1-1 | Paragraph number | 0014 |
| 1-3 | Description of deposition | |
| 1-3-1 | Depository name | International Patent Organism Depository (IPOD), National Institute of Advanced Industrial Science and Technology |
| 1-3-2 | Depository address | Central 6, 1-1-1Higashi, Tsukuba, Ibaraki 305-8566, Japan |
| 1-3-3 | Deposit date | Jan. 16, 2002 (16.01.2002) |
| 1-3-4 | Accession number | IPOD FERM BP-10094 |
| 1-5 | Designated states for these descriptions | All designated states |
| 2 | The following descriptions relate to the bacteria or biological materials described in detailed description of the invention. | |
| 2-1 | Paragraph numbers | 0009, 0015 |
| 2-3 | Description of deposition | |
| 2-3-1 | Depository name | International Patent Organism Depository (IPOD), National Institute of Advanced Industrial Science and Technology |
| 2-3-2 | Depository address | Central 6, 1-1-1Higashi, Tsukuba, Ibaraki 305-8566, Japan |
| 2-3-3 | Deposit date | May 6, 2003 (06.05.2003) |
| 2-3-4 | Accession number | IPOD FERM BP-10095 |
| 2-5 | Designated states for these descriptions | All designated states |
| 3 | The following descriptions relate to the bacteria or biological materials described in detailed description of the invention. | |
| 3-1 | Paragraph numbers | 0009, 0015 |
| 3-3 | Description of deposition | |
| 3-3-1 | Depository name | International Patent Organism Depository (IPOD), National Institute of Advanced Industrial Science and Technology |
| 3-3-2 | Depository address | Central 6, 1-1-1Higashi, Tsukuba, Ibaraki 305-8566, Japan |

| | | |
|---|---|---|
| | -continued | |
| 3-3-3 | Deposit date | May 6, 2003 (06.05.2003) |
| 3-3-4 | Accession number | IPOD FERM BP-10096 |
| 3-5 | Designated states for these descriptions | All designated states |
| 4 | The following descriptions relate to the bacteria or biological materials described in detailed description of the invention. | |
| 4-1 | Paragraph numbers | 0009, 0015 |
| 4-3 | Description of deposition | |
| 4-3-1 | Depository name | International Patent Organism Depository (IPOD), National Institute of Advanced Industrial Science and Technology |
| 4-3-2 | Depository address | Central 6, 1-1-1Higashi, Tsukuba, Ibaraki 305-8566, Japan |
| 4-3-3 | Deposit date | May 6, 2003 (06.05.2003) |
| 4-3-4 | Accession number | IPOD FERM BP-10097 |
| 4-5 | Designated states for these descriptions | All designated states |
| 5 | The following descriptions relate to the bacteria or biological materials described in detailed description of the invention. | |
| 5-1 | Paragraph numbers | 0009, 0015 |
| 5-3 | Description of deposition | |
| 5-3-1 | Depository name | International Patent Organism Depository (IPOD), National Institute of Advanced Industrial Science and Technology |
| 5-3-2 | Depository address | Central 6, 1-1-1Higashi, Tsukuba, Ibaraki 305-8566, Japan |
| 5-3-3 | Deposit date | May 6, 2003 (06.05.2003) |
| 5-3-4 | Accession number | IPOD FERM BP-10098 |
| 5-5 | Designated states for these descriptions | All designated states |
| | Space for receiving office | |
| 0-4 | This sheet is received together with international application. Yes/No | |
| 0-4-1 | Authorized staff member | |
| | Space for international bureau | |
| 0-5 | Receipt date of this sheet by international bureau | |
| 0-5-1 | Authorized staff member | |

The invention claimed is:

1. An additive for feeds comprising (A) *Lactobacillus equi* cells and (B) cells of at least one bacterium selected from the group consisting of: *Lactobacillus salivarius* YIT0479 strain (accession number: FERM BP-10095), *Lactobacillus reuteri* YIT0480 strain (accession number: FERM BP-10096), *Lactobacillus crispatus* YIT0481 strain (accession number: FERM BP-10097), and *Lactobacillus johnsonii* YIT0482 strain (accession number: FERM BP-10098); and wherein the number of cells of (A) *Lactobacillus equi* is 5 to 25% of the total amount of cells (A) and (B) present in the additive.

2. An additive for feeds according to claim 1, further comprising (C) at least one antibiotic selected from the group consisting of: ceftriaxone sodium; kanamycin sulfate; dihydrostreptomycin; sulfamonomethoxine; Bactramin; gentamicin; ofloxacin; cefalotin sodium; ampicillin; oxytetracycline hydrochloride; and benzylpenicillin.

3. A feed comprising the additive for feeds according to claims 1 or 2.

4. An additive for feeds according to claims 1 or 2, wherein the total amount of cells of (A) and (B) present in the additive is from more than $1\times10^9$ cells to less than $5\times10^{10}$ cells per horse per day.

5. An additive for feeds according to claims 1 or 2, wherein the number of cells of (A) *Lactobacillus equi* is 10 to 20% of the total amount of cells (A) and (B) present in the additive.

* * * * *